(12) United States Patent
Nguyen

(10) Patent No.: US 6,551,271 B2
(45) Date of Patent: Apr. 22, 2003

(54) ASYMMETRICAL BIDIRECTIONAL STEERABLE CATHETER

(75) Inventor: Frank Nguyen, Chino Hills, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 09/846,732

(22) Filed: Apr. 30, 2001

(65) Prior Publication Data
US 2002/0161330 A1 Oct. 31, 2002

(51) Int. Cl.[7] .............................................. A61M 37/00
(52) U.S. Cl. .................................................... 604/95.04
(58) Field of Search ........................... 604/95.01, 95.04, 604/525–529; 600/146

(56) References Cited

U.S. PATENT DOCUMENTS

| | | | |
|---|---|---|---|
| 4,986,257 A | * 1/1991 | Chikama | 600/146 |
| 5,328,467 A | 7/1994 | Edwards et al. | |
| 5,477,856 A | 12/1995 | Lundquist | |
| 5,549,542 A | 8/1996 | Kovalcheck | |
| 5,820,591 A | * 10/1998 | Thompson et al. | 604/529 |
| 5,897,529 A | 4/1999 | Ponzi | |
| 6,024,739 A | 2/2000 | Ponzi et al. | |
| 6,066,125 A | * 5/2000 | Webster, Jr. | 604/95.04 |

* cited by examiner

Primary Examiner—Anhtuan T. Nguyen

(74) Attorney, Agent, or Firm—Christie, Parker & Hale, LLP

(57) ABSTRACT

A bidirectional steerable catheter is provided that can be deflected to form two different curves, i.e., two curves each having a different radius of curvature. The catheter comprises an elongated, flexible tubular catheter body having proximal and distal ends and a lumen extending therethrough. A tip section is provided at the distal end of the catheter body. The tip section comprises a flexible plastic tubing having at least first and second off-axis lumens extending therethrough. A control handle is attached to the proximal end of the catheter body. A first puller wire extends through the lumen of the catheter body and the first off-axis lumen of the tip section. The first puller wire has a distal end anchored in the tip section and a proximal end anchored to the control handle. A second puller wire extends through the lumen of the catheter body and the second off-axis lumen of the tip section. The second puller wire has a distal end anchored in the tip section and a proximal end anchored to the control handle. A first compression coil extends through the lumen of the catheter body in surrounding relation to the first puller wire. The first compression coil has a distal end anchored in the catheter body or in the first off-axis lumen of the tip section at a first anchor position. A second compression coil extends through the lumen of the catheter body in surrounding relation to the second puller wire and into the second off-axis lumen. The second compression coil has a distal end anchored in the second off-axis lumen of the tip section at a second anchor position that is distal to the first anchor position. By this design, the radius of curvature of each curve achieved by deflection of the tip section is controlled by the anchor position of the compression coil surrounding the appropriate puller wire.

8 Claims, 8 Drawing Sheets

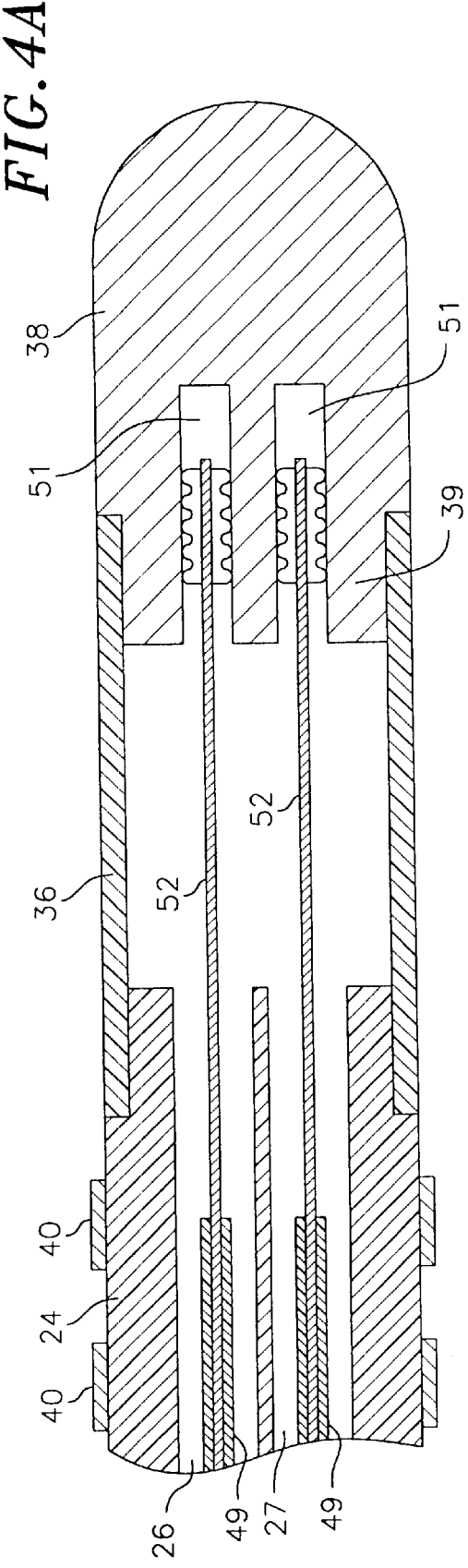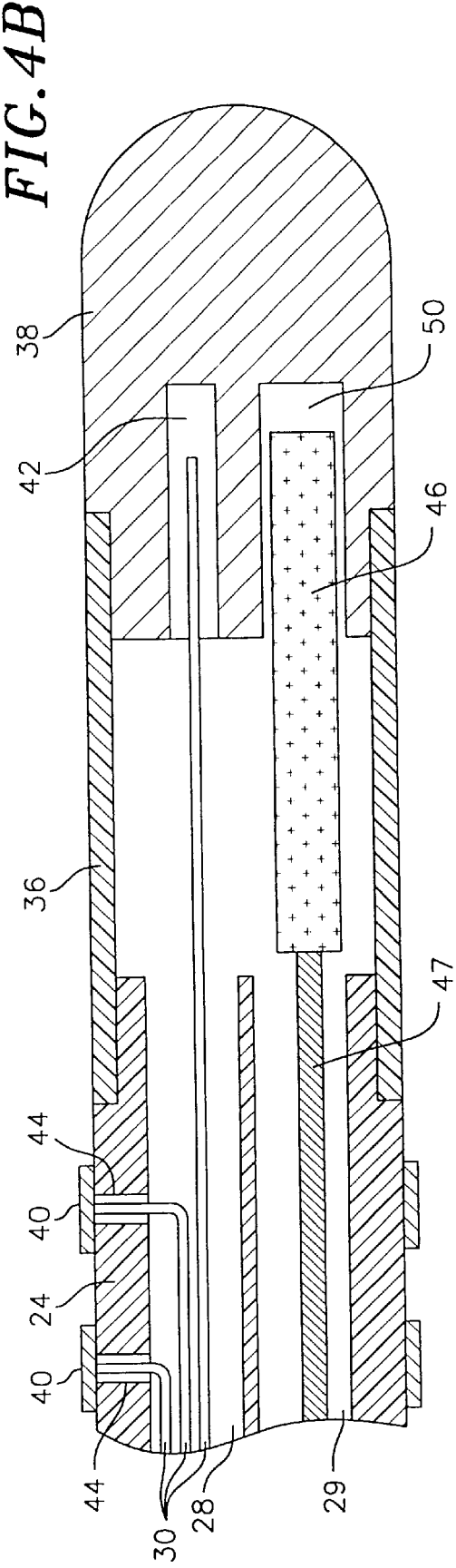

US 6,551,271 B2

ASYMMETRICAL BIDIRECTIONAL STEERABLE CATHETER

FIELD OF THE INVENTION

The present invention relates to a bidirectional steerable catheter that permits asymmetrical deflection.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Steerable catheters are generally well-known. For example, U.S. Pat. No. RE 34,502 describes a catheter having a control handle comprising a housing having a piston chamber at its distal end. A piston is mounted in the piston chamber and is afforded lengthwise movement. The proximal end of the catheter body is attached to the piston. A puller wire is attached to the housing and extends through the piston and through the catheter body. The distal end of the puller wire is anchored in the tip section of the catheter. In this arrangement, lengthwise movement of the piston relative to the housing results in deflection of the catheter tip section.

Bidirectional steerable catheter, i.e., a catheter that can be deflected in two directions, typically opposing directions, are also known. For example, U.S. Pat. No. 6,210,407 discloses a bidirectional steerable catheter having two puller wires extending through the catheter. The distal ends of the puller wires are anchored to opposite sides of the tip section of the catheter. A suitable bidirectional control handle is provided that permits longitudinal movement of each puller wire to thereby allow deflection of the catheter in two opposing directions.

It is often desirable to provide a bidirectional steerable catheter that can be deflected to form two different curves, i.e., two curves each having a different radius of curvature. Such designs are often preferred by physicians because it gives them a choice of curves during a procedure. Existing catheters achieve this result by having two puller wires with distal ends anchored at different positions along the length of the catheter.

SUMMARY OF THE INVENTION

The present invention is directed to a bidirectional steerable catheter that can be deflected to form two different curves, i.e., two curves each having a different radius of curvature. In accordance with the present invention, the catheter comprises an elongated, flexible tubular catheter body having proximal and distal ends and a lumen extending therethrough. A tip section is provided at the distal end of the catheter body. The tip section comprises a flexible plastic tubing having at least first and second off-axis lumens extending therethrough. A control handle is attached to the proximal end of the catheter body.

A first puller wire extends through the lumen of the catheter body and the first off-axis lumen of the tip section. The first puller wire has a distal end anchored in the tip section and a proximal end anchored to the control handle. A second puller wire extends through the lumen of the catheter body and the second off-axis lumen of the tip section. The second puller wire has a distal end anchored in the tip section and a proximal end anchored to the control handle.

A first compression coil extends through the lumen of the catheter body in surrounding relation to the first puller wire. The first compression coil has a distal end anchored in the catheter body or in the first off-axis lumen of the tip section at a first anchor position. A second compression coil extends through the lumen of the catheter body in surrounding relation to the second puller wire and into the second off-axis lumen. The second compression coil has a distal end anchored in the second off-axis lumen of the tip section at a second anchor position that is distal to the first anchor position. By this design, the radius of curvature of each curve achieved by deflection of the tip section is controlled by the anchor position of the compression coil surrounding the appropriate puller wire.

DESCRIPTION OF THE DRAWINGS

These and other features of the advantages of the present invention will be better understood by reference to the following detailed description when considered in conjunction with the accompanying drawings wherein:

FIG. 4A is a side cross-sectional view of the distal end of the tip section showing the small off-axis lumens and puller wires.

FIG. 4B is a side cross-sectional view of the distal end of the tip section showing the large off-axis lumens, sensor, sensor cable and electrode lead wires.

DETAILED DESCRIPTION

Figure 1:
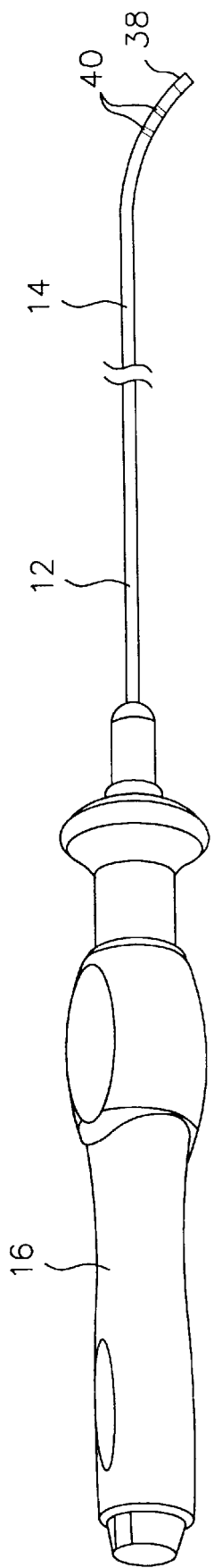
FIG. 1 is a side view of an embodiment of the catheter of the invention.

In a particularly preferred embodiment of the invention, there is provided a steerable bidirectional electrode catheter that can be deflected in two different directions to form two different curves, i.e., two curves each having a different radius of curvature. As shown in FIG. 1, the catheter 10 comprises an elongated catheter body 12 having proximal and distal ends, a tip section 14 at the distal end of the catheter body 12, and a control handle 16 at the proximal end of the catheter body 12.

Figure 2:
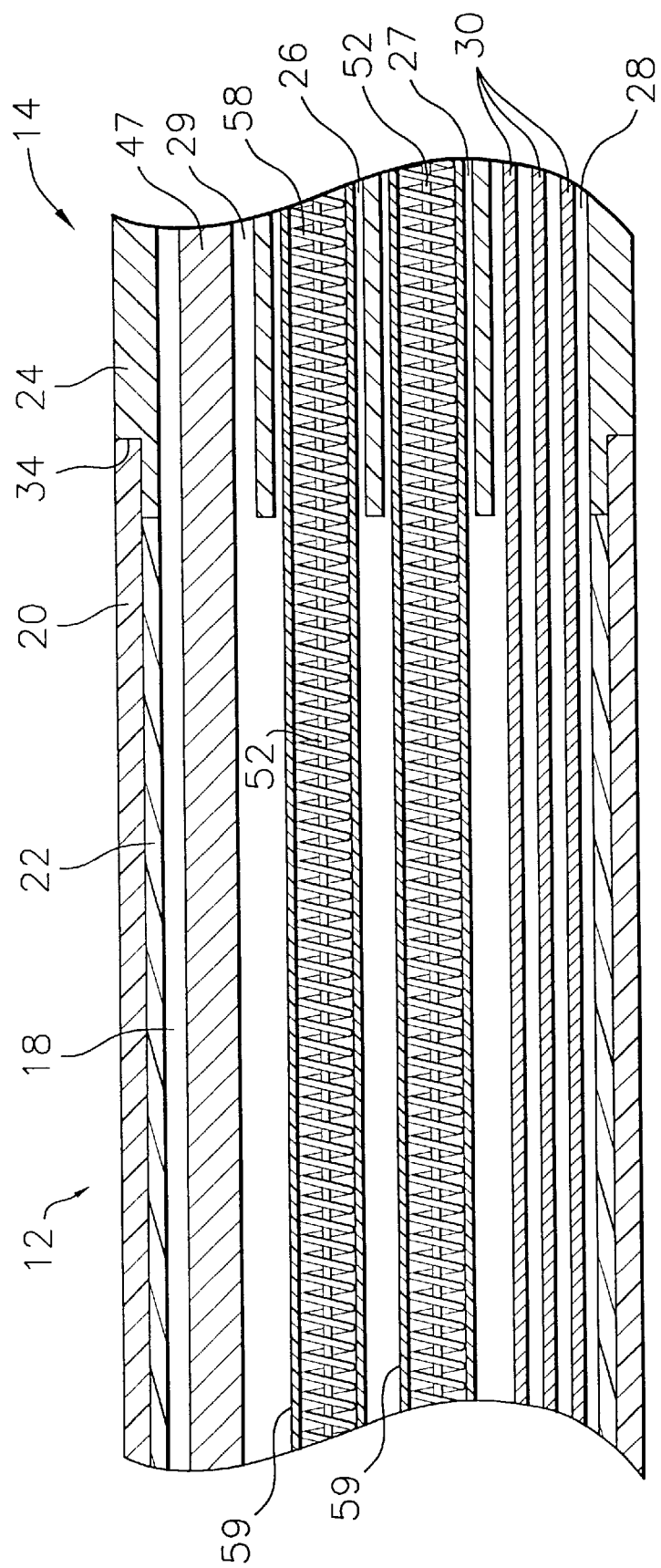
FIG. 2 is a side cross-sectional view of the junction of the catheter body and tip section of an embodiment of a catheter according to the invention.
Figure 3:
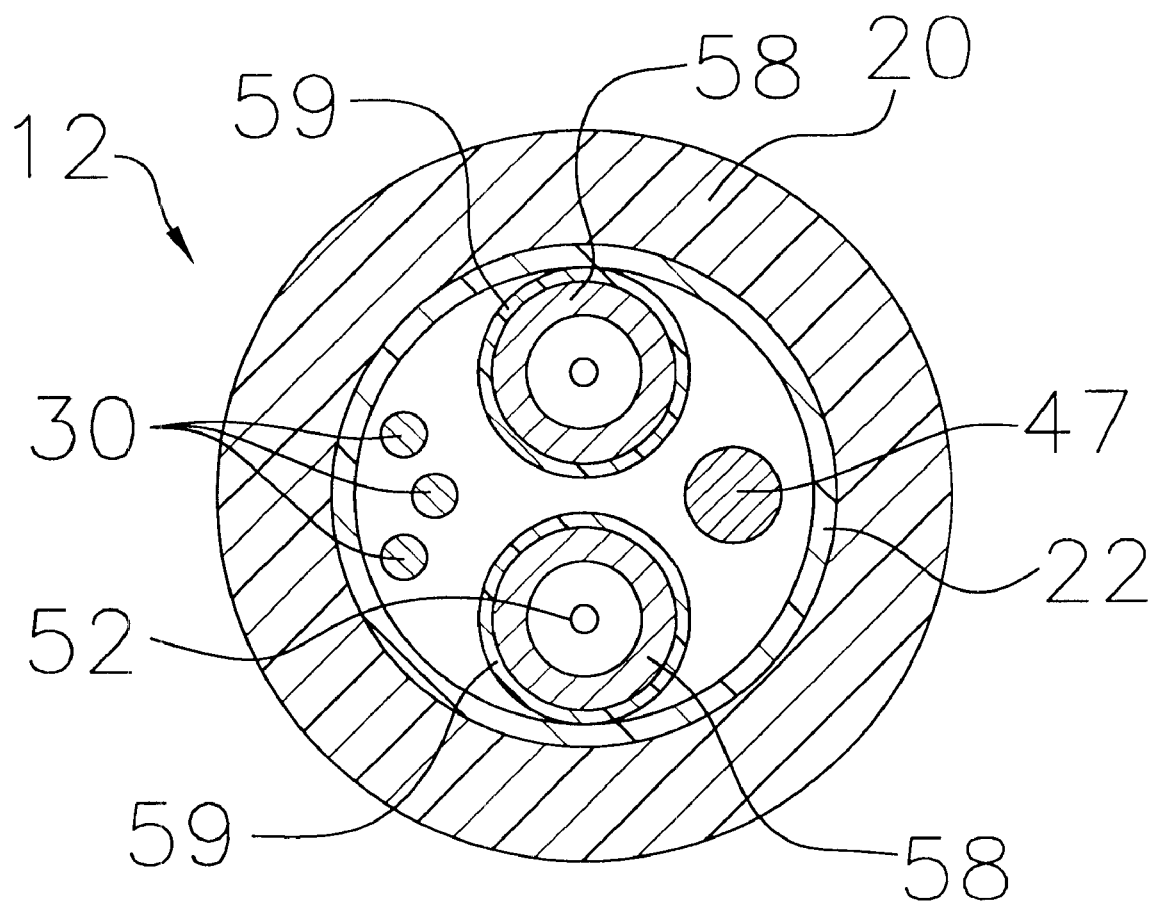
FIG. 3 is a transverse cross-sectional view of the catheter body shown in FIG. 2 taken along line 3—3.

As shown in FIGS. 2 and 3, the catheter body 12 comprises an elongated tubular construction having a single axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 preferably comprises an imbedded braided mesh of stainless steel or the like to increase torsional stiffness of the catheter body 12 so that when the control handle 16 is rotated the tip section 14 will rotate in a corresponding manner.

The overall length and diameter of the catheter 10 may vary according to the application. A presently preferred catheter 10 has an overall length of about 48 inches. The outer diameter of the catheter body 12 is not critical, but is preferably no more than about 8 french. The inner surface of the outer wall 20 is lined with a stiffening tube 22, which can be made of any suitable material, preferably nylon or polyimide. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter 10 has an outer diameter of about 0.092 inch and a central lumen 18 diameter of about 0.052 inch. If desired, the stiffening tube 22 can be omitted.

Figure 5:
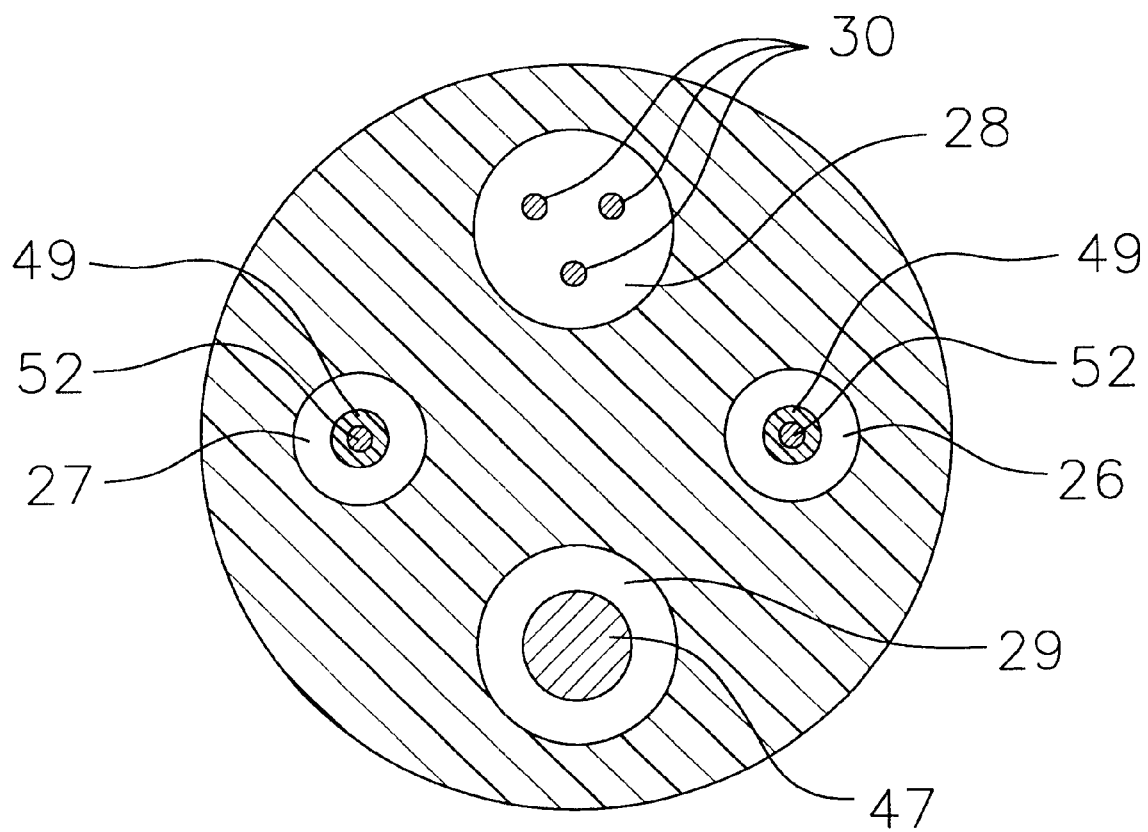
FIG. 5 is a transverse cross-sectional view of the tip section along line 5—5.

As shown in FIGS. 4 and 5, the tip section 14 comprises a short section of flexible tubing 24 having four off-axis lumens. The flexible tubing 24 is made of a suitable non-toxic material that is preferably more flexible than the catheter body 12. A presently preferred material for the tubing 24 is braided polyurethane, i.e., polyurethane with an embedded mesh of braided stainless steel or the like, similar to the outer wall 20 of the catheter body 12. The outer diameter of the tip section 14, like that of the catheter body 12, is preferably no greater than about 8 french, more preferably about 6½ french or less.

First and second small off-axis lumens 26 and 27 of approximately equal size are positioned in opposing quadrants of the tubing 24. First and second large off-axis lumens 28 and 29 of approximately equal size that are larger than the first and second small off-axis lumens 26 and 27 are positioned in opposing quadrants of the tubing 24 between the first and second small off-axis lumens. In the depicted embodiment, the four lumens are generally evenly-spaced about the axis of the flexible tubing 24. In a particularly preferred embodiment, the catheter has a diameter of approximately 7 French, the first and second small off-axis lumens 26 and 27 each have a diameter of approximately 0.17 to 0.18 inch, and the first and second large off-axis lumens 28 and 29 each have a diameter of approximately 0.26 to 0.27 inch. As will become more apparent, the precise number and size of the lumens in the tip section is not critical to the present invention and can vary as desired, so long as at least two off-axis lumens are provided.

A preferred means for attaching the catheter body 12 to the tip section 14 is illustrated in FIG. 2. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. Preferably a small distance, e.g., about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and, while the stiffening tube is under compression, a first glue joint (not shown) is made between the stiffening tube and the outer wall 20 by a fast drying glue, e.g. Super Glue®. Thereafter a second glue joint is formed between the proximal ends of the stiffening tube 22 and outer wall 20 using a slower drying but stronger glue, e.g., polyurethane. If desired, a spacer (not shown) can be provided within the catheter body 12 between the distal end of the stiffening tube 22 and the proximal end of the tip section 14, as described in more detail in U.S. Pat. No. 5,897,529, the disclosure of which is incorporated herein by reference.

As shown in FIG. 4, the distal end of the tip section 14 carries a tip electrode 38. The length of the tip electrode 38 is not critical and depends on the particular application for which the catheter is to be used. Typical tip electrodes 38 have an exposed length, e.g., length outside of the tubing 24, ranging from about 2 mm to about 6 mm.

The tip electrode 38 is connected to the tubing 19 of the tip section 14 by means of a plastic housing 36, preferably made of polyetheretherketone (PEEK). The distal end of the tip electrode 36 forms a stem 39, which fits inside the distal end of the plastic housing 36 and is bonded to the housing by polyurethane glue or the like. The proximal end of the plastic housing 36 is bonded with polyurethane glue or the like to the distal end of the tubing 19 of the tip section 14.

Mounted along the length of the tip section 14 near the distal end are two ring electrodes 40 spaced apart from each other so that their edges do not touch. The length of each ring electrode 40 is also not critical, but preferably ranges from about 1 mm to about 3 mm. Similarly, the distance between the ring electrodes 40 is not critical, but can typically range from about 2 mm to about 6 mm. More or less ring electrodes can be provided if desired. If desired the ring electrodes 40 and/or tip electrode 38 can be eliminated altogether, depending on the particular application for the catheter. If desired, ring electrodes can be mounted on the plastic housing 36 in addition to or instead of on the tubing 19 of the tip section 14.

The tip electrode 38 and ring electrode 40 are each connected to a separate lead wire 30. Each electrode lead wire 30 extends through the first large off-axis lumen 28 in the tip section 14, through the central lumen 18 in the catheter body 12 and through the control handle 16. The proximal end of each lead wire 30 extends is connected to an appropriate connector, which can be plugged into or otherwise connected to a suitable monitor, source of energy, etc.

The lead wires 30 are connected to the tip electrode 38 and ring electrode 40 by any conventional technique. Connection of a lead wire 30 to the tip electrode 38 is preferably accomplished by mounting the distal end of the lead wire in a first blind hole 42 in the tip electrode and attached by solder or the like.

Connection of a lead wire 30 to a ring electrode 40 is preferably accomplished by first making a small hole 44 through the tubing 24. Such a hole 44 can be created, for example, by inserting a needle through the tubing 24 and heating the needle sufficiently to form a permanent hole. A lead wire 30 is drawn through the hole 44 by using a microhook or the like. The end of the lead wire 30 is then stripped of any coating and welded to the underside of the ring electrode 40, which is then slid into position over the hole 44 and fixed in place with polyurethane glue or the like.

Additionally, a location sensor 46, preferably an electromagnetic location sensor, is contained within the distal end of the tip section 14. Suitable electromagnetic sensors for use with the present invention are described, for example, in U.S. Pat. Nos. 6,201,387,5,558,091, 5,443,489, 5,480,422, 5,546,951, 5,568,809, and 5,391,199 and International Publication No. WO 95/02995, the disclosures of which are incorporated herein by reference. The electromagnetic location sensor 46 has its proximal end mounted in a second blind hole 50 in the tip electrode 36 and fixed by polyurethane glue or the like. The remainder of the sensor 46 is contained within the plastic housing 36 that is mounted between the tip electrode 36 and the flexible tubing 19 of the tip section. If desired, the plastic housing 36 can be eliminated, and a portion of the sensor 46 is mounted in the distal end of the plastic tubing 19.

The electromagnetic sensor 46 is connected to an electromagnetic sensor cable 47, which extends through the second large off-axis lumen 29 of the tip section 14, through the catheter body 12, and into the control handle 16. The electromagnetic sensor cable 47 comprises multiple wires encased within a plastic covered sheath. The sensor cable 47 is connected to a circuit board (not shown), which amplifies the signal received from the electromagnetic sensor 46 and transmits it to a computer in a form understandable by the computer. Preferably the circuit board is contained within the control handle. Alternatively, the circuit board can be provided outside the control handle with the sensor cable extending out the proximal end of the handle.

For deflection of the tip section 14, two puller wires 52 extend through the catheter 10. Each puller wire 52 extends from the control handle 16, through the central lumen 18 in the catheter body 12 and into one of the small off-axis lumens 26 and 27 of the tubing 24. The proximal end of each puller wire 52 is anchored within the control handle 16 and the distal end of each puller wire is anchored within the tip section 14.

Each puller wire 52 is made of any suitable metal, such as stainless steel or Nitinol. Preferably each puller wire 52 has a coating, such as a coating of Teflon® or the like. Each puller wire 52 has a diameter preferably ranging from about 0.006 inch to about 0.0010 inch. Preferably both of the puller wires 52 have the same diameter.

Each puller wire 52 is anchored near the distal end of the tip section 14. In the embodiment depicted in FIG. 4, the distal ends of the puller wires 52 are both anchored in blind holes 51 in the tip electrode 38 by a welding or the like.

Figure 6:
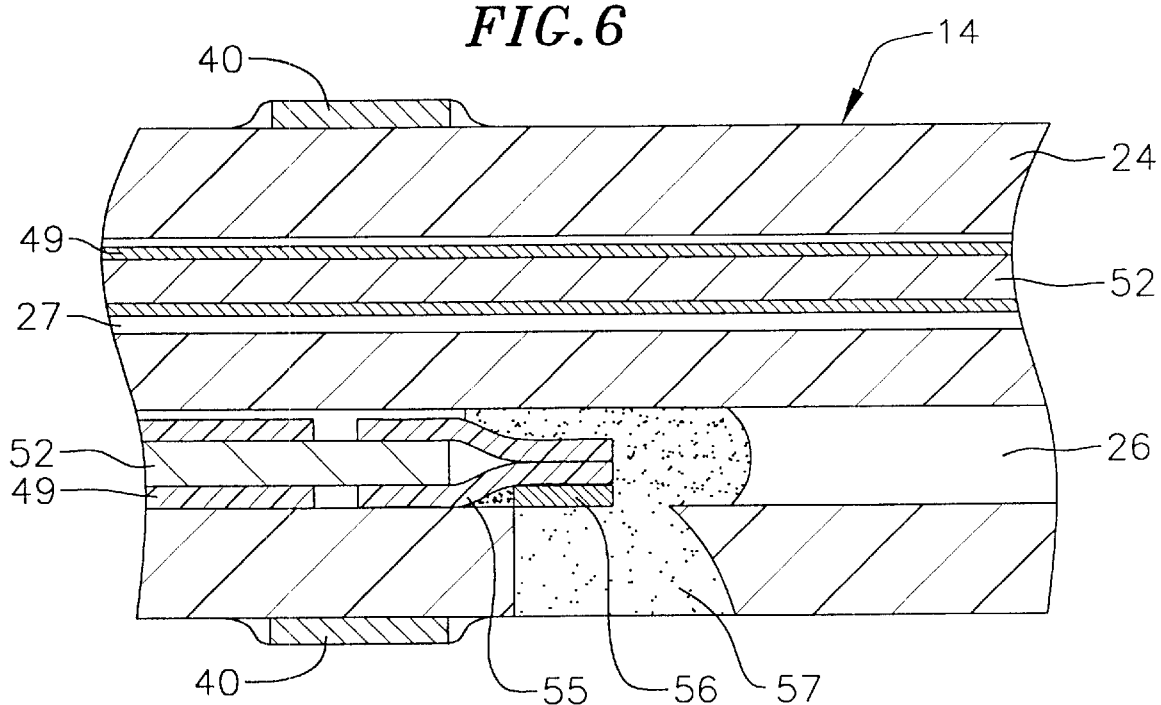
FIG. 6 is a transverse cross-sectional view of a catheter tip section according to the invention where the puller wires are anchored to the side walls of the tip section.
Figure 7:
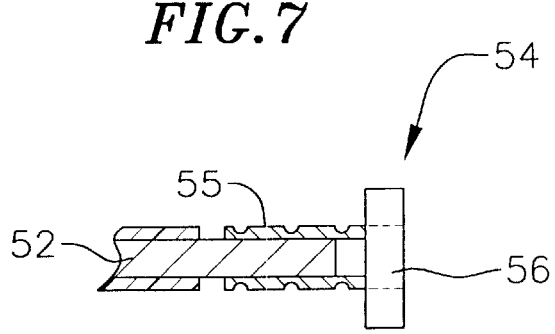
FIG. 7 is a longitudinal cross-sectional view of a preferred puller wire T-bar anchor.
Figure 8:
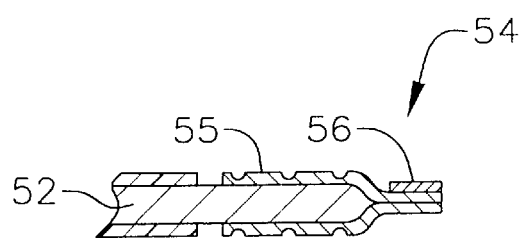
FIG. 8 is a longitudinal cross-sectional view of the puller wire T-bar anchor of FIG. 7 rotated 90° to show the cross-piece on end.

Alternatively, one or both puller wires 52 can be anchored to the side wall of the tip section 14. As shown in FIGS. 6 to 8, the puller wire 52 extending through the first small off-axis lumen 26 is attached to the side wall of the tubing 24 by means of an anchor 54 fixedly attached to the distal end of the puller wire 52. The anchor 54 is formed by a metal tube 55, e.g., a short segment of hypodermic stock, that is fixedly attached, e.g. by crimping, to the distal end of the puller wire 52. The tube 55 has a section that extends a short distance beyond the distal end of the puller wire 52. A cross-piece 56 made of a small section of stainless steel ribbon or the like is soldered or welded in a transverse arrangement to the distal end of the metal tube 55 which is flattened during the operation. This creates a T-bar anchor 54. A notch 57 is created in the side of the tubing 24 of the tip section 14, resulting in an opening in the first small off-axis lumen 26 carrying the puller wire 52. The cross piece 56 lies transversely within the notch 57. Because the length of the ribbon forming the cross-piece 56 is longer than the diameter of the notch 57 into the first small off-axis lumen 26, the anchor 54 cannot be pulled completely into the off-axis lumen. The notch 57 then sealed with polyurethane glue or the like to give a smooth outer surface. The glue flows into the first small off-axis lumen 26 to fully secure the anchor 54. Other means for anchoring the puller wires 52 in the tip section 14 would be recognized by those skilled in the art and are included within the scope of the invention.

In the depicted embodiment, the distal ends of the puller wires 52 are attached to opposite sides of the tubing 24 of the tip section 14. This design permits deflection of the tip section 14 in opposing directions. Alternatively, the puller wires 52 can be attached at different locations about the circumference of the tip section 14 that are not opposing, permitting deflection in two different directions, although not opposing directions.

Figure 9:
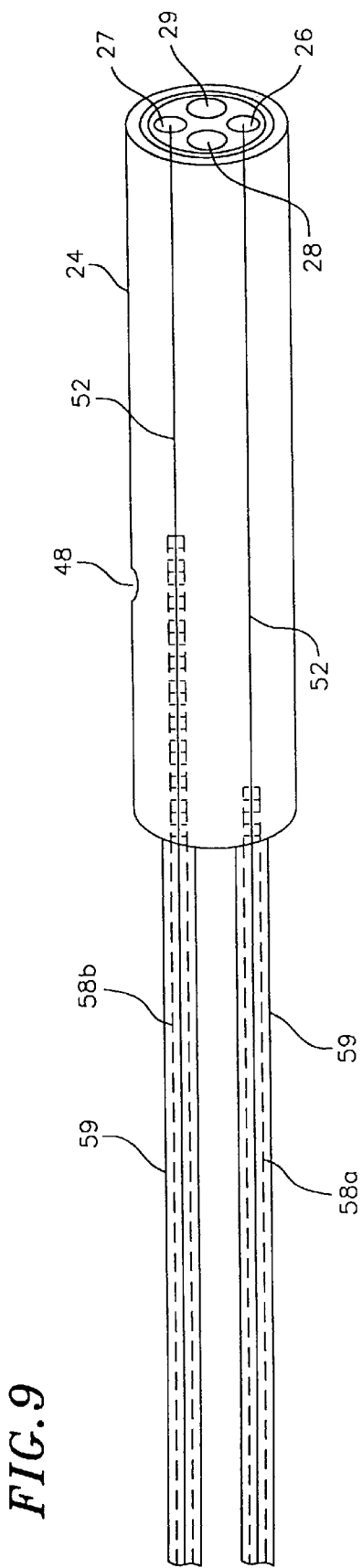
FIG. 9 is a side schematic view of the tip section showing the relative positioning of the long and short compression coils.

The catheter 10 further comprises two compression coils 58, each in surrounding relation to a corresponding puller wire 52, as shown in FIGS. 2 and 9. Each compression coil 58 is made of any suitable metal, such as stainless steel. Each compression coil 58 is tightly wound on itself to provide flexibility, i.e., bending, but to resist compression. The inner diameter of each compression coil 58 is slightly larger than the diameter of its associated puller wire 52. For example, when a puller wire 52 has a diameter of about 0.007 inch, the corresponding compression coil 58 preferably has an inner diameter of about 0.008 inch. The coating on the puller wires 52 allows them to slide freely within the compression coils 58.

The outer surface of each compression coil 58 is covered along most of its length by a flexible, non-conductive sheath 59 to prevent contact between the compression coil 58 and the lead wires 30 within the central lumen 18 of the catheter body 12. A non-conductive sheath 59 made of thin-walled polyimide tubing is presently preferred. Each sheath 59 is glued at its proximal and distal ends to its respective compression coil 58 with polyurethane glue or the like.

At the distal end of the catheter body 12, the two compression coils 58 are positioned in diametric opposition within the stiffening tube 22 so that they can be aligned with the two small off-axis lumens 26 and 28 in the tip section 14. The compression coils 58 and stiffening tube 22 are sized so that the compression coils fit closely and slidably within the stiffening tube. With this design, the lead wires 30 and sensor cable 47 distribute themselves around the two compression coils 58 without misaligning the coils.

The compression coils 58 each extend into a different small off-axis lumen 26 or 27 along with an associated puller wire 52. Each compression coil 58 is anchored at its proximal end to the proximal end of the stiffening tube 22 in the catheter body 12 by a glue joint (not shown). When a stiffening tube 22 is not used, each compression coil 58 is anchored directly to the outer wall 20 of the catheter body 12.

The distal end of each compression coil 58 is anchored in its corresponding small off-axis lumen 26 and 27 by a glue joint (not shown). The compression coils 58 have different lengths. The short compression coil 58a extends just inside the first small off-axis lumen 26, e.g., a distance ranging from about 5 mm to about 10 mm. The short compression coil 58a is anchored in place with polyurethane glue or the like. In a preferred manufacturing procedure, a mandrel (not shown) is inserted into the distal end of the short compression coil 58a and then glue is applied to the distal end of the short compression coil. The mandrel prevents the glue from blocking the inside of the compression coil. The distal end of the short compression coil 58a is then inserted into the first small off-axis lumen 26, the mandrel is removed, and one of the puller wires 52 is then inserted into the compression coil.

The long compression coil 58b extends into the second small off-axis lumen 27 with its distal end positioned distal to the distal end of the short compression coil 58a. The long compression coil 58b can be introduced into the tip section 14 in a manner similar to the short compression coil 58a. In a preferred embodiment, the long compression coil 58b is anchored at two positions within the tip section 14. A glue joint is provided approximately 1 to 2 mm short of the distal end of the long compression coil 58b by forming an anchor hole 48 in the side of the tubing 19 of the tip section 14. Additionally, the long compression coil 58b is glued within the proximal end of the tip section 14 at the same location that the distal end of the short compression coil 58a is anchored.

Figure 10:
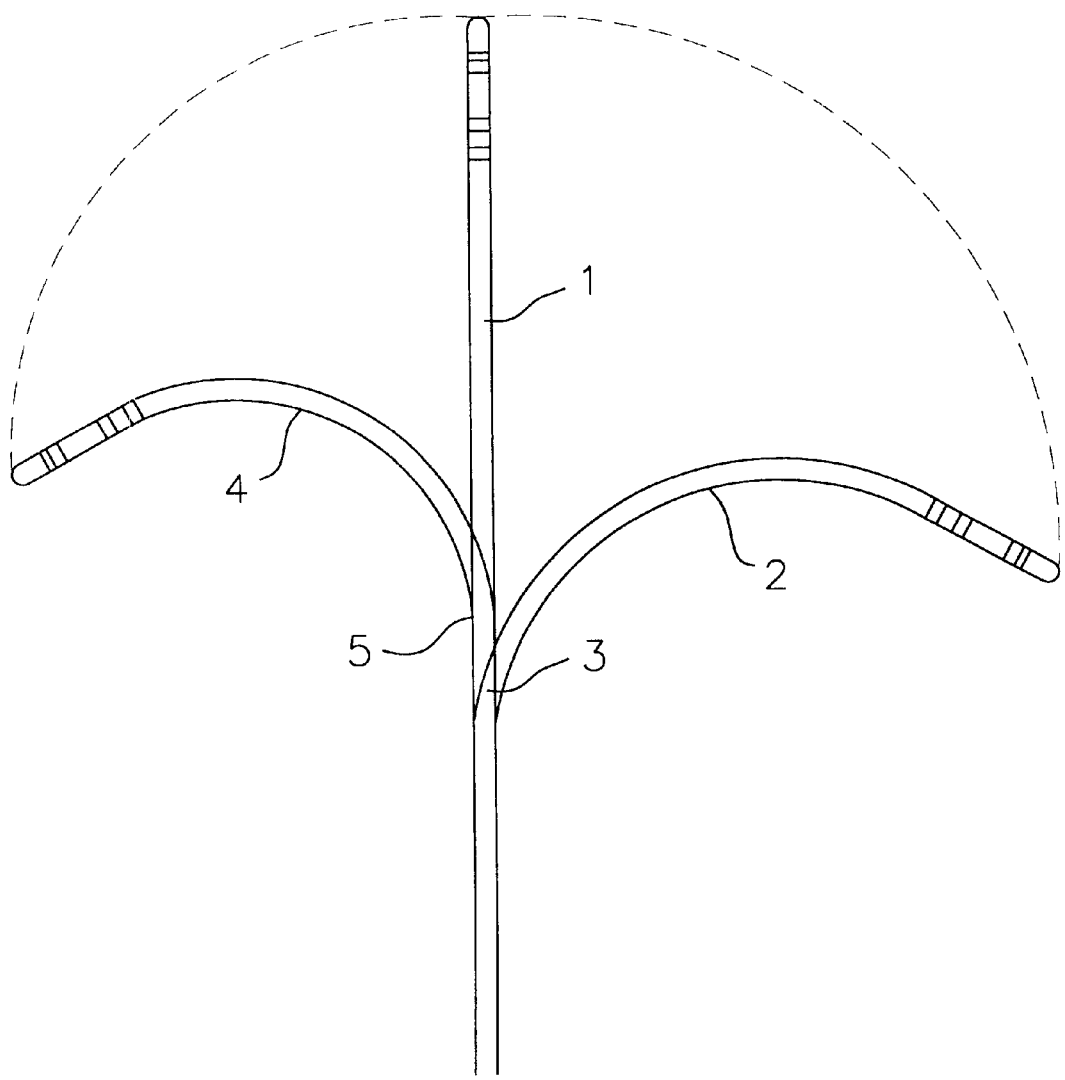
FIG. 10 is a side schematic view of the tip section showing the different curves that are formed upon deflection of the puller wires extending through the long and short compression coils.

By having the compression coils 58 extend to different positions along the length of the tip section 14, the catheter can be deflected in two different directions to create two different curves, i.e., two curves each having a different radius of curvature, as shown in FIG. 10. When the tip section 14 is not deflected, i.e., in a neutral position 1, it is generally straight. Longitudinal movement of the puller wire that extends in the first small off-axis lumen 26 (i.e., the puller wire surrounded by the short compression coil 58a) will cause the tip section 14 to deflect to create a first curve 2 having a first radius of curvature. The first curve 2 will bend from a first position 3 along the length of the tip section 14 generally corresponding to the distal end of the short compression coil 58a. Longitudinal movement of the puller wire that extends in the second small off-axis lumen 27 (i.e., the puller wire surrounded by the long compression coil 58b) will cause the tip section 14 to deflect to create a second curve 4 having a second radius of curvature. The second curve 4 will bend from a second position 5 along the length of the tip section 14 generally corresponding to the distal end of the long compression coil 58b. Thus, the second position 5 is distal to the first position 3, and the radius of curvature of the first curve 2 is greater than the radius of curvature of the second curve 4. As a result, a single deflectable catheter can be used to create two different curves.

The anchor positions of the distal ends of the compression coils 58 will define the curves that are formed by deflection of the tip section 14. The precise anchor positions are not critical and will depend on the desired curves for a particular application. In a preferred embodiment, the distance between the distal ends of the compression coils 58 ranges from about 0.5 cm to about 2.5 cm, more preferably from about 1 cm to about 2 cm.

Within the small off-axis lumens 26 and 27, each puller wire 32 is surrounded by a plastic sheath 49, preferably made of Teflon®. The plastic sheathes 49 prevent the puller wires 52 from cutting into the wall of the tip section 14 when the tip section is deflected. Preferably the distal end of each sheath 49 ends near the distal end of each puller wire 52, and the proximal end of each sheath 49 ends just distal to the distal end of each compression coil 58.

Longitudinal movement of a puller wire 52 relative to the catheter body 12, which results in deflection of the tip section 14, is accomplished by suitable manipulation of the control handle 16. A suitable bidirectional control handle for use in the present invention is described in copending application Ser. No. 09/822,087, filed Mar. 30, 2001 and entitled "Steerable Catheter with a Control Handle Having a Pulley Mechanism", the disclosure of which is incorporated herein by reference. Other suitable bidirectional control handles are described in U.S. Pat. Nos. 6,123,699, 6,171,277, 6,183,463, and 6,198,974, the disclosures of which are incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A bidirectional steerable catheter comprising:
   an elongated, flexible tubular catheter body having proximal and distal ends and a lumen extending therethrough;
   a tip section at the distal end of the catheter body, the tip section having proximal and distal ends and comprising a flexible plastic tubing having at least first and second off-axis lumens extending therethrough;
   a control handle at the proximal end of the catheter body;
   a first puller wire extending through the lumen of the catheter body and the first off-axis lumen of the tip section, and having a distal end anchored in the tip section at an anchor position and a proximal end anchored to the control handle;
   a second puller wire extending through the lumen of the catheter body and the second off-axis lumen of the tip section, and having a distal end anchored in the tip section at an anchor position and a proximal end anchored to the control handle;
   a first compression coil extending through the lumen of the catheter body in surrounding relation to the first puller wire, the first compression coil having a distal end anchored in the catheter body or in the first off-axis lumen of the tip section at a first anchor position; and
   a second compression coil extending through the lumen of the catheter body in surrounding relation to the second puller wire and into the second off-axis lumen, the second compression coil having a distal end anchored in the second off-axis lumen of the tip section at a second anchor position that is distal to the first anchor position and proximal to the anchor position of the first puller wire.

2. A catheter according to claim 1, wherein the distal end of the first puller wire is attached to one side of the tip section and the distal end of the second puller wire is attached to the opposite side of the tip section.

3. A catheter according to claim 1, wherein the distal end of one puller wire is attached to the distal end of the catheter body at a first position and the distal end of the other puller wire is attached to the distal end of the catheter body at a second position proximal to the first position.

4. A catheter according to claim 1, wherein the distal end of the first compression coil is anchored in the first off-axis lumen of the tip section.

5. A catheter according to claim 1, wherein the distal end of the first compression coil is anchored in the first off-axis lumen of the tip section a distance ranging from about 5 mm to about 10 mm from about proximal end of the tip section.

6. A catheter according to claim 1, wherein the distance between the first anchor position and the second anchor position ranges from about 0.5 cm to about 2.5 cm.

7. A catheter according to claim 1, wherein the distance between the first anchor position and the second anchor position ranges from about 1 cm to about 2 cm.

8. A catheter according to claim 1, further comprising:
   a first plastic sheath in surrounding relation to the first puller wire and having a proximal end that is distal to the distal end of the first compression coil; and
   a second plastic sheath in surrounding relation to the second puller wire and having a proximal end that is distal to the distal end of the second compression coil.

* * * * *